United States Patent [19]

Tamm et al.

[11] 4,175,863

[45] Nov. 27, 1979

[54] GRAPHITE TUBE ATOMIZER FOR FLAMELESS ATOMIC ABSORPTION SPECTROSCOPY

[75] Inventors: Rolf G. Tamm, Salem; Günter Grosser; Toma Tomoff, both of Uberlingen, all of Fed. Rep. of Germany

[73] Assignee: Bodenseewerk Perkin-Elmer & Co. GmbH, Uberlingen, Fed. Rep. of Germany

[21] Appl. No.: 787,036

[22] Filed: Apr. 13, 1977

[30] Foreign Application Priority Data

Apr. 23, 1976 [DE] Fed. Rep. of Germany ....... 2617928

[51] Int. Cl.² .................. G01J 3/30; H01R 13/54; H01R 13/62
[52] U.S. Cl. ...................................... 356/312; 339/35
[58] Field of Search ............... 356/85; 339/35, 117 P; 91/462, 466, 464

[56] References Cited

U.S. PATENT DOCUMENTS

| 2,052,976 | 9/1936 | Harcourt | 91/466 |
|---|---|---|---|
| 3,277,420 | 10/1966 | Council | 339/35 |
| 4,022,530 | 5/1977 | Braun et al. | 356/85 |

FOREIGN PATENT DOCUMENTS 2501507 7/1976 Fed. Rep. of Germany ............. 356/85

OTHER PUBLICATIONS

Hedges, C.S., "Practical Fluid Power Control-Electrical & Fluidic" Womack Educational Pubs., Dallas, Texas, 1971, pp. 9-12.
Stewart et al. "ABC's of Hydraulic Circuits," Howard W. Sams & Co. Inc., The Bobbs-Merrill Co., Inc., 1973.

*Primary Examiner*—John K. Corbin
*Assistant Examiner*—Wm. H. Punter
*Attorney, Agent, or Firm*—S. A. Giarratana; F. L. Masselle; E. T. Grimes

[57] ABSTRACT

A graphite tube atomizer for flameless atomic absorption spectroscopy includes a graphite tube disposed to permit passage of a measuring beam therethrough. The graphite tube is engaged at opposite ends by annular contact pieces which are coupled to a source of electrical current. The contact pieces are supported in housing portions which serve to surround the graphite tube and provide a chamber into which cooling gasses can be admitted. The cooling gasses also serve to reduce deterioration of the graphite tube. The housing portions are selectively movable either toward or away from each under the power of a drive mechanism. The housings may be urged by the drive mechanism toward each other so the contacts mounted thereon are in selectable pressure engaging contact opposite ends of the graphite tube.

5 Claims, 3 Drawing Figures

GRAPHITE TUBE ATOMIZER FOR FLAMELESS ATOMIC ABSORPTION SPECTROSCOPY

BACKGROUND OF THE INVENTION

The invention relates to a graphite tube atomizer for flameless atomic absorption spectroscopy which includes a support for a graphite tube having two annular contact pieces disposed to permit passage of a measuring beam along the axis of the graphite tube. The contact pieces are electrically connected to current conducting cables and mounted on a relatively moveable, mechanically biased, cooled housing portions.

One known graphite tube atomizer is described, for example, in U.S. patent application Ser. No. 608,558 which was filed on Aug. 28, 1975 now U.S. Pat. No. 4,022,530. The graphite tube atomizer theredescribed has two housing portions each of which consist of a cooling jacket as well as a socket both of which are mounted in an adjustable manner on a base. A contact piece is supported inside the cooling jacket and has a coolant passage within it. The cooling jacket of one housing portion is axially moveable relative to the socket and biased towards the other housing portion by means of a pair of annular cup springs. The contact pieces and the cooling jackets are also annular so as to form a center aperture for the passage of a measuring beam. A graphite tube is inserted between the contact pieces by pushing one cooling jacket with the associated contact against the action of the annular cup springs thereby permitting the graphite tube to be interposed between the contact pieces. When the cooling jacket is released, the graphite tube is held resiliently between the contact pieces by the bias provided by the annular cup springs. The cooling jackets and contact pieces are mounted in electrically insulating manner and are connected to a current supply. The bias provided by the annular cup spring provides contact pressure between the contact pieces and the graphite tube thus providing a low resistance contact so that heating current can pass through the contact pieces and the graphite tube. In operation, a sample to be tested is introduced into the graphite tube through a radial bore. The sample is decomposed and atomized by directing a high current through the graphite tube. The absorbtion to which the measuring beam passing along the axis of the graphite tube is subjected in the "atomic cloud" thus formed serves as a measure of a quantity of the element being looked for in the sample.

The above described atomic absorption apparatus accommodates varying length graphite tubes as the socket of one housing portion is axially displaceable on a pair of guide rods relative to the other housing portion. If a shorter tube is installed in the apparatus, the socket is accordingly displaced to accommodate its shorter length.

In prior art arrangements of the type described above, consecutive analyses are usually carried out in the device using a single graphite tube. After each analysis, the graphite tube is heated and the formed atomic cloud is flushed from the tube by an inert gas flow therethrough. This inert gas flow protects the graphite tube from oxygen and prevents combustion of the tube itself. Thereafter, the next sample is fed through the radial bore of the graphite tube. Exchange of graphite tubes is only required after a rather large number of analyses when the tube has become worn in spite of the inert gas flow which tends to prevent such wear.

Slight length differences between graphite tubes do occur and can be compensated for by the yielding of the annular cup springs. The same applies to the thermal dilation of the graphite tube. However, the spring bias of the annular cup springs and thus the contact pressure between the contact pieces and the graphite tube is dependent on the length of the graphite tube and on the thermal dilation thereof. Accordingly, the apparatus described above is subject to some variation as a function of tube length and the thermal dilation which occurs.

The above described apparatus is reasonably satisfactory in environments where graphite tube exchange is not required, however, there are applications where such graphite tube changes are required frequently. An example of such an application is in analyzing fine dusts in gases by means of atomic absorption spectroscopy. In such an application, the fine dust contained in the gas is deposited electrostaticly directly in a graphite tube. The graphite tube is then placed in a graphite tube atomizer and subsequently heated until the dust particles are atomized (see German Patent Specification No. 24 01 873, German Patent Specification No. 24 35 091). In such applications or similar applications, the graphite tube is exchanged for each analysis. For flameless atomic absorbtion spectrometers of the type described in the above pending U.S. patent application Ser. No. 608,558, even the aid of a special noncontaminating tool is of little help in placing a graphite tube into the atomizer because its physical design makes replacing the graphite tube quite difficult.

In applications where frequent exchange of graphite tubes is required, it is quite common that the length of the graphite tubes does vary somewhat. When utilized in an apparatus of the type described in the above mentioned U.S. patent application, Ser. No. 608,558, different contact pressures occur between tests due to differing tube length so that some tests may be made with inappropriate electrical contact resistance between the contacts and the end of the graphite tube. Other times, the bias of the annular cup springs is too large which runs the risk of damaging the fragile graphite tubes.

In view of the foregoing difficulties, it is the primary objective of the invention to provide a graphite tube atomizer for flameless atomic absorption spectroscopy wherein the tube is held in a mechanism which permits easy tube changing without giving rises to the problems associated with prior art graphite tube atomizers.

It is still a further objective of the invention to provide a graphite tube atomizer for atomic absorption spectroscopy which has a tube holding means including contacts which are urged towards opposite ends of the tube and maintained in constant pressure contact with the tube.

In achieving these and other objectives of the invention, the graphite tube atomizer of the present invention is designed so that exchanging the graphite tube is facilitated as compared to the approach for changing graphite tubes in prior art mechanisms. In particular, it is possible to place the graphite tube into the tube atomizer without contamination. Furthermore, a well-defined contact pressure between the graphite tube and contact pieces is insured independently of the graphite tube length.

The stated objectives of the invention are achieved by a graphite tube support mechanism including a reversable drive means which is operable to move the housing portions away from each other in one driving direction to permit removal of the graphite tube and moveable towards each other in the other driving direction to permit a graphite tube to be interposed therebetween. In addition, the drive means provides contact pressure between the contact pieces and the graphite tube which is selectable regardless of the tube length thereby avoiding the problem of high resistance contact as well as the problem of excessive pressure on the fragile tube.

The drive means in its preferred form is a pneumatic cylinder or other drive means capable of selective movement in opposite directions and exerting a selectable force. Preferably, the first housing portion of the graphite tube atomizer is stationary and the second housing portion is moveable relative thereto. When the drive means is a pneumatic cylinder, it is attached to the first housing portion with the double-acting piston being coupled to the second housing portion. Then, the force with which the contact pieces are pressed against the graphite tube depends only on the pressure in the pneumatic cylinder and is independent of tube length or the position of the housing portions which encircle the graphite tube.

The foregoing and other objects, advantages and features of the invention are described further below with reference to the accompanying drawings wherein.

DETAILED DESCRIPTION

Figure 1:
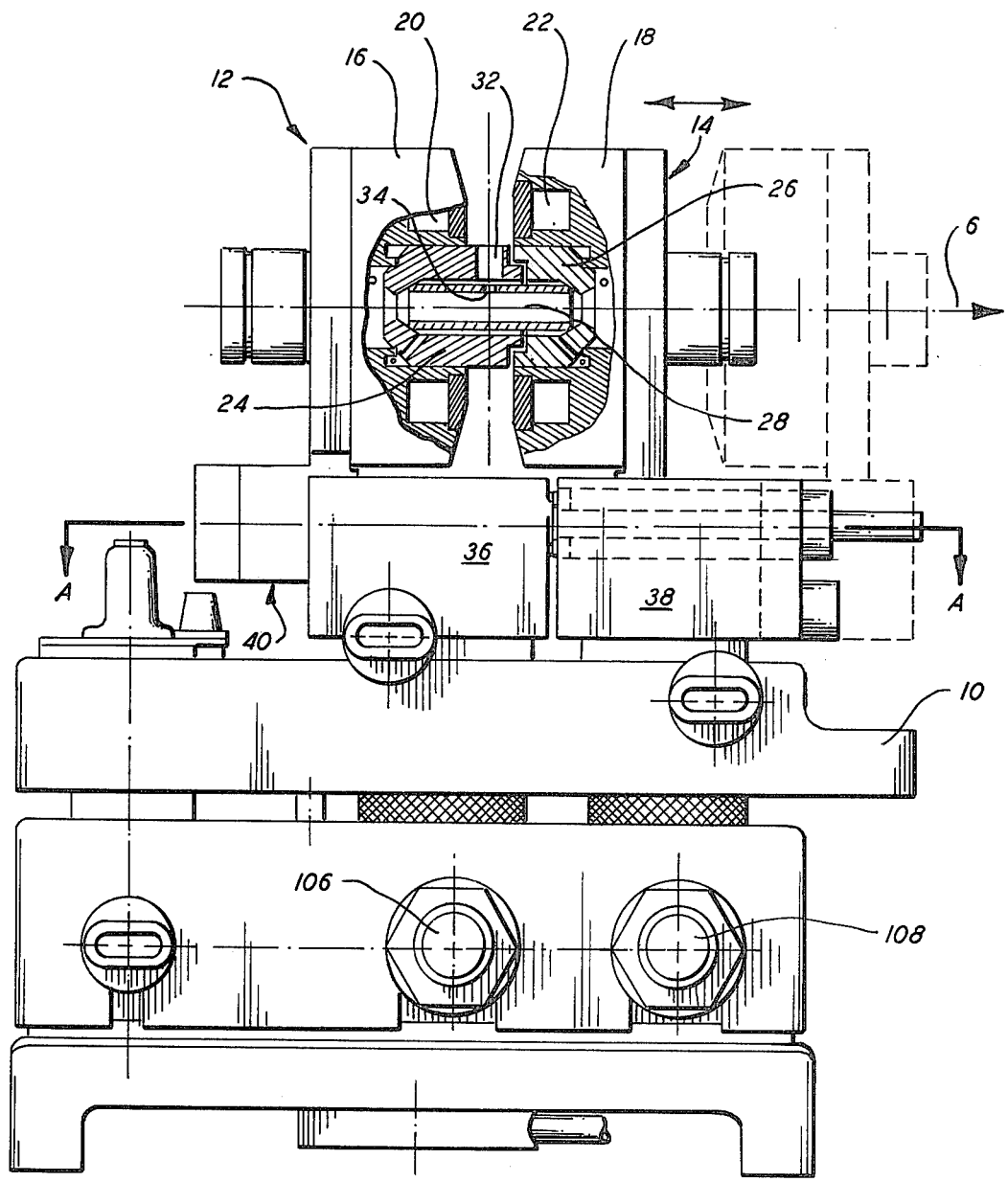
FIG. 1 is an elevational view of a graphite tube atomizer in its closed state with a graphite tube held therein.

Two housing portions 12 and 14 are arranged on a base 10. Each of the housing portions comprises a cooling jacket 16 or 18, respectively, in which a coolant passage 20 or 22, respectively, is formed. The cooling jacket 16 or 18 and coolant passage 20 or 22 are of annular shape. A contact piece 24 or 26, respectively, is located in each cooling jacket 16, 18 in good electric and heat conducting contact with the cooling jacket. The contact pieces 24 and 26 are also annular. A graphite tube 28 is held between the contact pieces 24 and 26 and is surrounded thereby, said contact pieces forming a jacket around the graphite tube. A measuring beam 6 passes along the axis of the graphite tube 28 through the graphite tube 28, through the contact pieces 24 and 26 and through the cooling jackets 16 and 18. A sample may be fed into the graphite tube 28 through a radial bore 34 of the graphite tube 28.

As indicated hereinbefore a sample, however, may also be deposited on the inner surface of the graphite tube 28 prior to the placing of the graphite tube 28 into the graphite tube atomizer.

Apart from this the construction is similar to that of the German Patent Specification 2,413 782 which corresponds to the above identified U.S. patent application Ser. No. 608,558.

The two cooling jackets 16 and 18 are each mounted in a socket 36 or 38, respectively. Socket 36 of the housing portion 12 is mounted stationarily, though adjustably, on the base 10. The housing portion 14 with the socket 38 is movable relative to the housing portion 12 to the right in FIG. 1 into the position indicated in dashed lines. This is done by means of a drive mechanism 40, which can best be seen from FIG. 2.

The drive mechanism 40 preferably comprises a pneumatic cylinder with a cylinder block 42, which has a cylinder chamber 44 on one side and a piston rod passage 46 on the other side coaxial with respect to the cylinder chamber 44. A sleeve 48 is supported coaxially within the cylinder chamber 44 and defines an annular passage 50 together with the wall of the cylinder chamber 44. The sleeve is supported sealingly adjacent the outer, i.e. lefthand in FIG. 2, end face of the cylinder chamber 44, the sealing being effected by an O-ring 51, and ends at a distance from the inner end face of the cylinder chamber 44. A double-acting piston 52, which comprises a body 54 and a pair of washer seals 56, 58 drawn thereon, is guided in the sleeve 48. A piston rod 60 is coupled to the piston 52. The piston rod 60 extends through the piston rod passage 46 and is sealingly guided to the outside of the cylinder block 42. The sealing is effected by a seal 62.

The cylinder block 42 is firmly held with its section containing the cylinder chamber 44 in the socket 36 of the housing portion 12 and is insulated by the sleeve 53. Instead of the sleeve 53, the necessary insulation may also be achieved by an appropriate coating of the cylinder 42. With its section containing the piston rod passage 46, the cylinder block extends into a cylindrical recess 64 in the socket 38 of the housing portion 14. Near the base of this recess 64, the piston rod 60 is coupled to the socket 38 by means of locking bar 66 and groove 68.

A guide rod 70 is supported in the socket 36 by means of two isolating bushings 72, 74. The socket 38 is guided for longitudinal movement through ball circulation bushings on the guide rod 70, which extends parallel to the piston rod 60.

Figure 2:
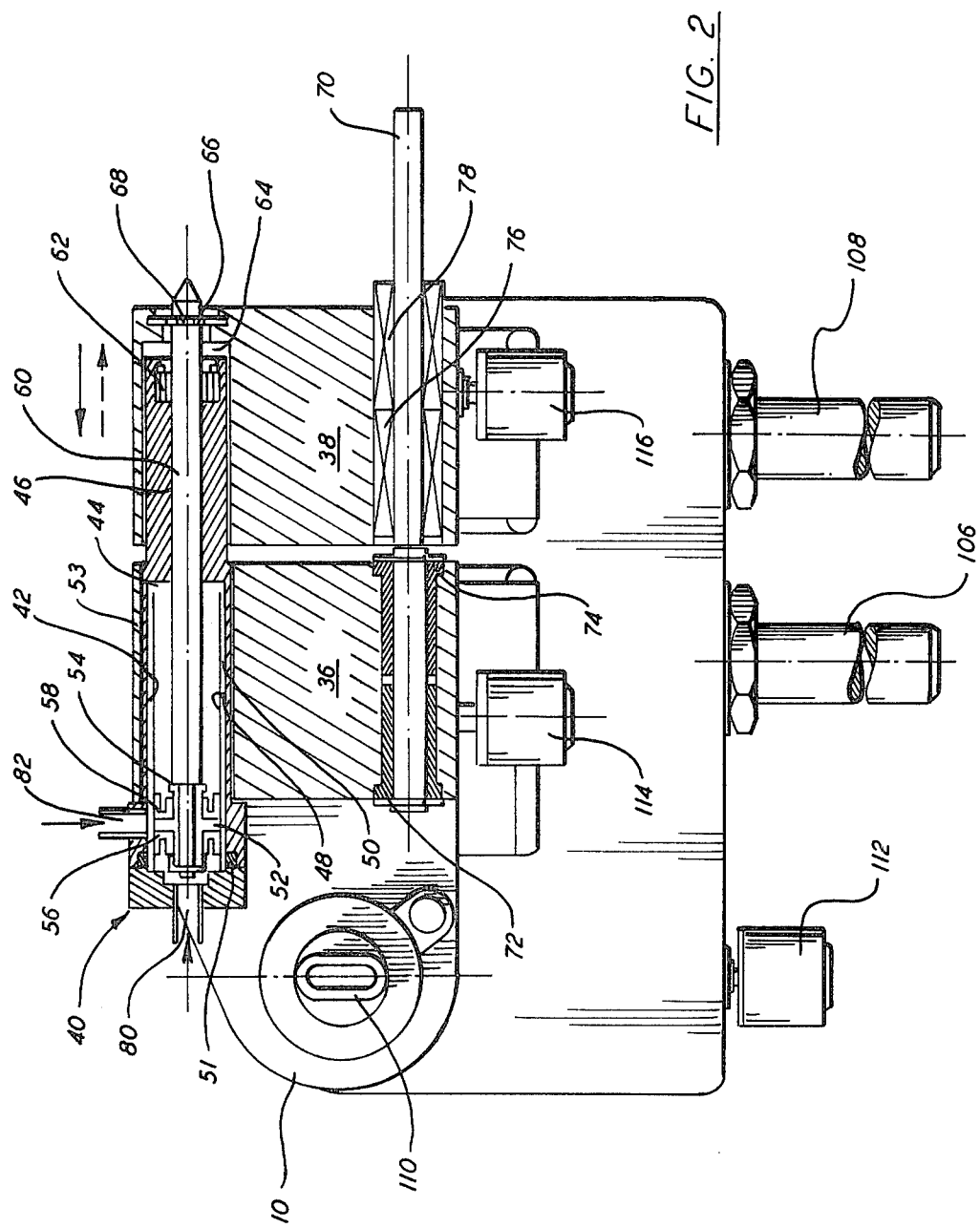
FIG. 2 is a sectional view of the drive mechanism arrangement taken along section line A—A of FIG. 1.

A first pressurizing gas port 80 opens into the end face of the cylinder chamber 44 on the lefthand side of FIG. 2. A second pressurizing gas port 82 opens into the annular passage 50. When pressurized gas is applied to the pressurizing gas port 80, the piston 52 will be moved to the right in FIG. 2. Thus the housing portion 14 will be moved to the right in FIG. 1 and 2 by the piston rod 60 to the position shown in dashed lines in FIG. 1. Now the graphite tube 28 can be removed conveniently, and a new graphite tube can be laid into the jacket shaped contact piece 24. If subsequently pressurized gas is directed to the pressurizing gas port 82, this pressurized gas will flow through the annular passage 50 and between the end of the sleeve 48 and the inner right end face of the cylinder chamber 44, and will urge the piston 52 and thereby the housing portion 14 to the left in FIG. 1, until the contact piece 26 engages the graphite tube 28. In this way the graphite tube 28 is pressed against the contact pieces 24 and 26 with a well-defined contact pressure determined by the pressure of the pressurized gases. This contact pressure is independent of the length of the graphite tube.

Figure 3:
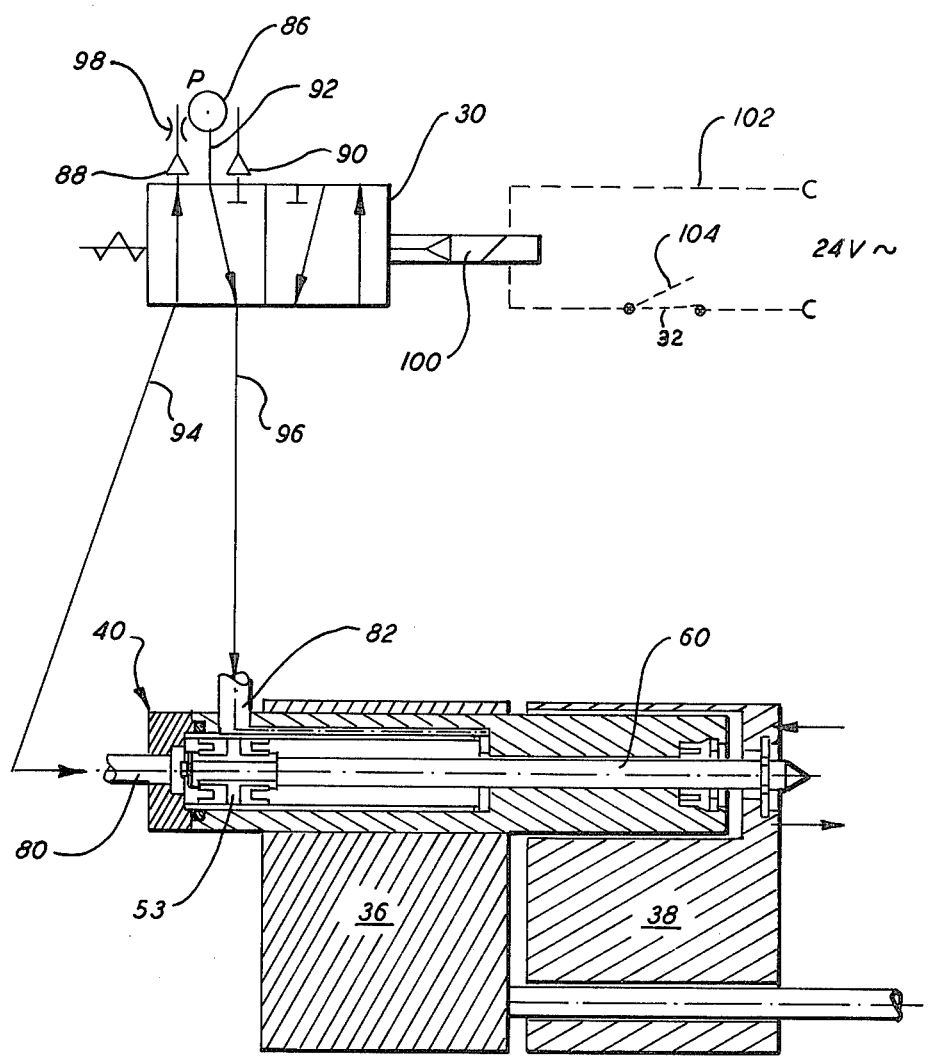
FIG. 3 illustrates schematically the control for the drive mechanism permitting it to go in either a forward or a reverse direction.

As can be seen from FIG. 3 the pressurizing gas ports 80 and 82 communicate with the free atmosphere or a source 86 of pressurized gas, respectively, through a 5/2 directional valve. The 5/2 directional valve has two venting ports 88, 90, a gas source port 92 and two ports 94, 96 communicating with the two pressurizing gas ports 80, 82 of the drive means 40. In one position of the 5/2 directional valve 30, the port 94 of the 5/2 directional valve 30 communicating with the pressurizing gas port 80 is connected to the venting port 88, which communicates with the atmosphere through a flow restrictor 98. The other port 96 is connected to the source 86 of pressurized gas through the gas source port 92. Now pressurized gas is directed to the righthand side in FIG. 3 of the piston 52 through the pressurizing gas port 82, so that the piston is moved to the left in FIG. 3 and the housing portions 12 and 14 are driven towards each other. The flow restrictor ensures that the speed of the housing portion 14 does not exceed a certain level, in order to avoid damage of the graphite tube. In the second position of the 5/2 directional valve 30 the pressurizing gas port 82 is vented to atmosphere without restriction, while the source 86 of pressurized gas is connected to the pressurizing gas port 80 through the gas source port 92 and the port 94.

The 5/2 directional valve 30 is arranged to be operated electromagnetically and has an energizing winding 100. A foot operated switch 104 is connected in the circuit 102 of the energizing winding. Upon operation of the foot operated switch 104 the 5/2 directional valve is moved away from the position shown into the second operative position, whereby the housing portions 12 and 14 are driven away from each other.

The inert gas, which is required for the graphite tube atomizer anyhow, may be used also as said pressurized gas.

Numerals 106 and 108 designate electrical terminals. Numerals 110, 112, 114, 116 are setting knobs for the adjustment of the graphite tube atomizer. The arrangement is similar to that shown in the German patent specification 24 13 782 which corresponds to the above identified U.S. Patent Application which is incorporated herein by reference and is therefore not described in detail. Instead of the illustrated rectilinear guidance of second housing portion 14 relative to the stationary first housing portion 12, an arrangement may be provided in which the housing portion 14 is arranged for rotary movement relative to the housing portion 12. Other modifications will occur to those skilled in the art which can be made without departing from the spirit and scope of the invention as defined in the claims.

What is claimed is:

1. A graphite tube atomizer for atomic absorption spectroscopy having a graphite tube disposed to permit passage of a measuring beam through the graphite tube, said atomizer comprising;

first and second housing portions,
   an annular contact piece carried by each of said first and second housing portions and adapted for electrical connection to current conducting cables,
   means for mounting said first housing portion for movement relative to said second housing portion,
   drive means connected to said first and second housing portions for selectively moving said first portion between a first position with its contact piece in contact with one end of the graphite tube under a substantially constant predetermined bearing pressure and a second position with its contact piece spaced from the one end of the graphite tube,
   said drive means including a cylinder housing carried by one of said first and second housing portions and a piston disposed in said cylinder housing and connected to the other of said first and second housing portions, and
   a source of gas under pressure,
   said drive means including valve means connected between said cylinder housing and said source of pressurized gas for selectively communicating gas from said source to said cylinder housing and thereby to relatively displace said cylinder housing and said piston to move said first housing portion between said first position and said second position and maintain the contact piece carried by said first housing portion in contact with the one end of the graphite tube under a substantially constant predetermined bearing pressure when said first housing portion is in said first position.

2. A graphite tube atomizer according to claim 1 wherein said cylinder housing comprises, a cylinder chamber disposed within said cylinder housing for guiding said piston,
   the walls of said cylinder chamber and said cylinder housing forming an annular passage communicating at one end of said cylinder housing with said cylinder chamber,
   a first pressurized gas port communicating with said cylinder chamber at the other end thereof,
   a second pressurized gas port communicating with said annular passage
   whereby when gas is applied to said second pressurized port said first portion is moved into said first position and when gas is applied to said first pressurized gas port said first portion is moved into said second position.

3. A graphite tube atomizer according to claim 2 wherein said valve means comprises.

a valve movable between first and second positions,
   spring means normally biasing said valve for movement into said first position,
   said valve having first and second ports connected to the atmosphere and a third port connected to said source of pressurized gas,
   first conduit means connecting said first pressurized gas port to said first port when said valve means is in said first position and to said third port when said valve is in said second position,
   second conduit means connecting said second pressurized gas port to said third port when said valve is in said first position and to said second port when said valve is in said second position.

4. A graphite tube atomizer according to claim 3 wherein said first port includes flow restricter means.

5. A graphite tube atomizer according to claim 4 wherein said control means comprises, an electromagnet connected to said valve for moving said valve from said first position into said second position, a source of voltage, and
   switch means for connecting said source of voltage and said electromagnet one to the other to actuate said valve means to move said valve from said first position into said second position against the bias of said spring.

* * * * *